United States Patent [19]
Auricchio et al.

[11] Patent Number: 5,935,160
[45] Date of Patent: Aug. 10, 1999

[54] LEFT VENTRICULAR ACCESS LEAD FOR HEART FAILURE PACING

[75] Inventors: Angelo Auricchio, Magdeburg, Germany; Rodney W. Salo, Fridley, Minn.; Bruce A. Tockman, Scandia, Minn.; Ronald W. Heil, Jr., Roseville, Minn.; Randy Westlund, Minneapolis, Minn.; Stuart R. Chastain, Shoreview, Minn.

[73] Assignee: Cardiac Pacemakers, Inc., St. Paul, Minn.

[21] Appl. No.: 08/787,274

[22] Filed: Jan. 24, 1997

[51] Int. Cl.[6] ................................. A61N 1/05
[52] U.S. Cl. ............................................. 607/122
[58] Field of Search .................. 607/120, 122, 607/123, 126, 127, 128

[56] References Cited

U.S. PATENT DOCUMENTS

| | | | |
|---|---|---|---|
| 4,559,951 | 12/1985 | Dahl et al. | 128/642 |
| 4,603,705 | 8/1986 | Speicher et al. | 128/786 |
| 4,608,986 | 9/1986 | Beranek et al. | 128/786 |
| 4,628,943 | 12/1986 | Miller | 128/785 |
| 4,630,611 | 12/1986 | King | 128/642 |
| 4,721,115 | 1/1988 | Owens | 128/713 |
| 4,727,877 | 3/1988 | Kallok | 128/419 |
| 4,777,955 | 10/1988 | Brayton et al. | 128/642 |
| 4,928,688 | 5/1990 | Mower | 128/419 |
| 4,932,407 | 6/1990 | Williams | 128/419 |
| 4,946,457 | 8/1990 | Elliott | 606/1 |
| 5,014,696 | 5/1991 | Mehra | 128/419 |
| 5,360,441 | 11/1994 | Otten | 607/122 |
| 5,431,683 | 7/1995 | Bowald et al. | 607/122 |
| 5,476,498 | 12/1995 | Ayers | 607/122 |
| 5,545,204 | 8/1996 | Cammilli et al. | 607/123 |
| 5,549,581 | 8/1996 | Lurie et al. | 607/122 |

*Primary Examiner*—Scott M. Getzow
*Attorney, Agent, or Firm*—Haugen and Nikolai, P.A.

[57] ABSTRACT

An elongated monopolar or bipolar coronary vein lead having a reduced outer diameter and especially adapted to be advanced into a selected coronary vein for delivering a pacing signal to a predetermined region of a patient's heart, such as the left ventricle. A method of using the lead for pacing a patient's heart in the treatment of heart failure is also described. The method for pacing the heart includes advancing the coronary vein lead through both the coronary sinus and into a selected coronary vein of a patient's heart, connecting the lead to an electrical pacing source and applying electrical stimulation to a particular chamber of the patient's heart via the implanted lead. The lead includes a flexible tip and transition ring that enhances the ability to guide the lead through the coronary veins.

35 Claims, 7 Drawing Sheets

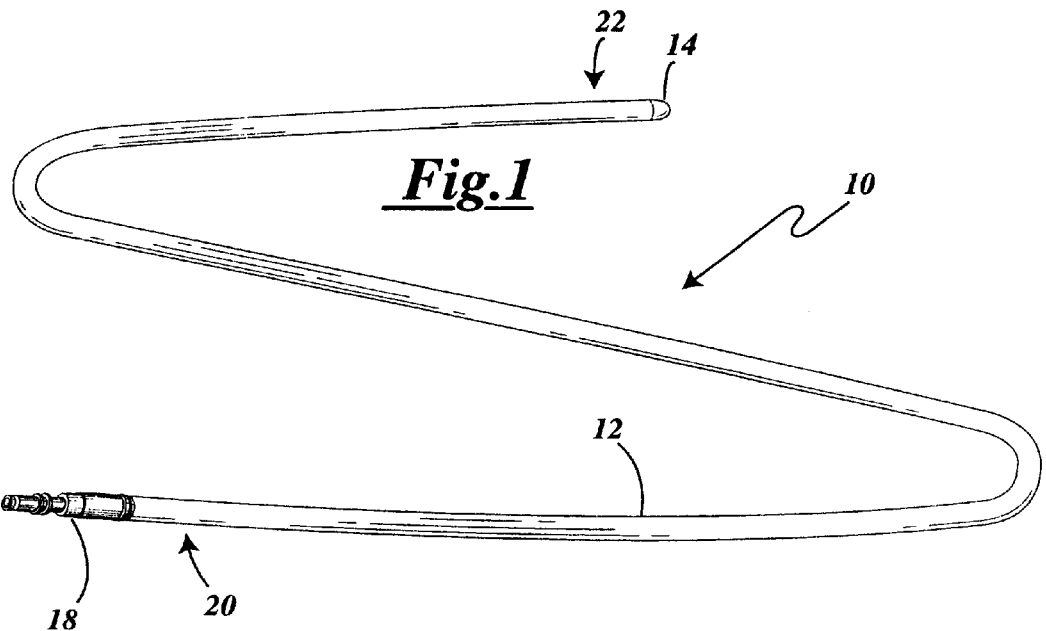
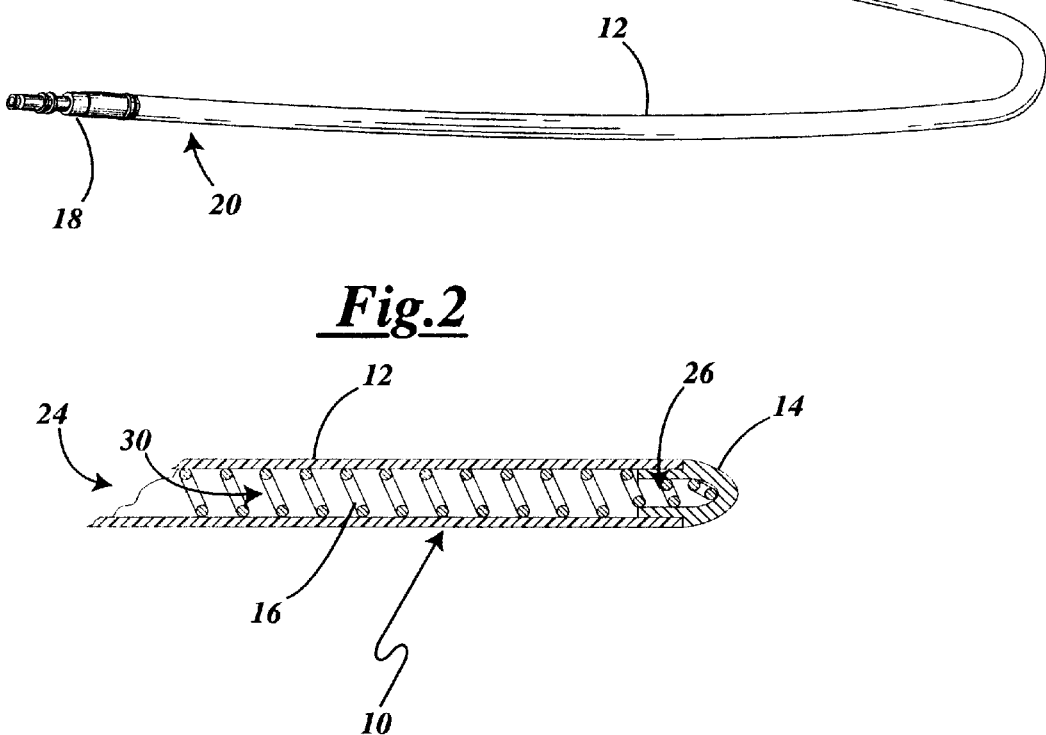
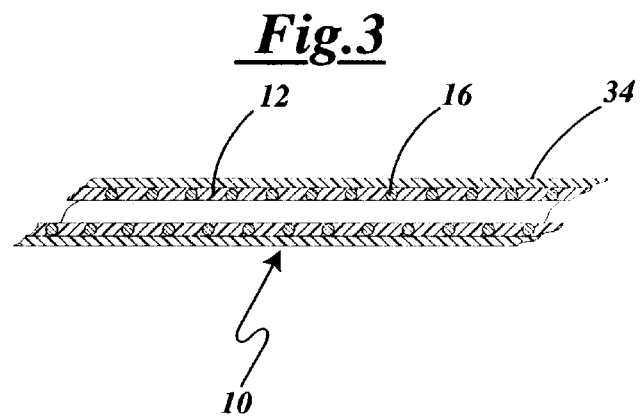

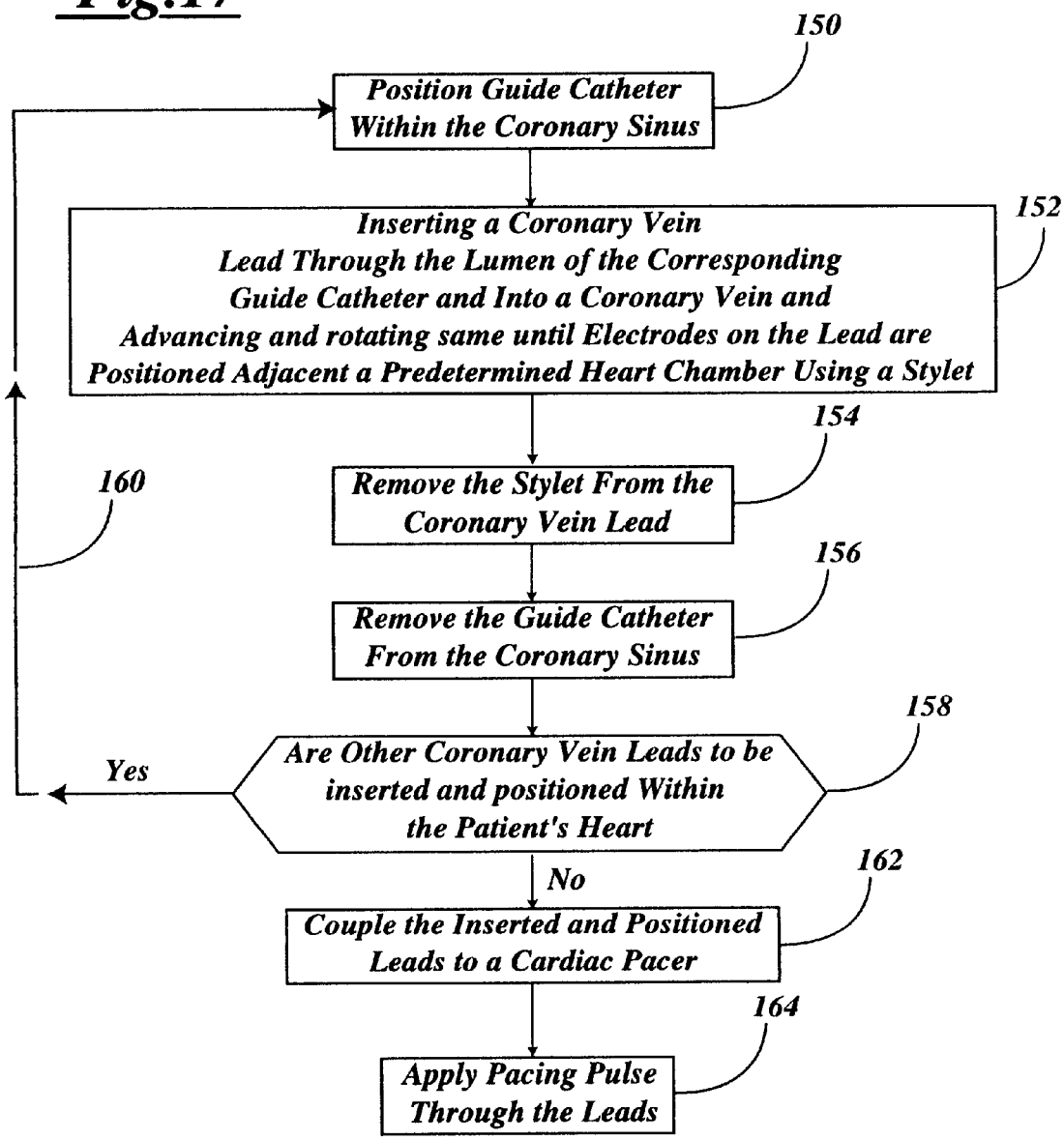

LEFT VENTRICULAR ACCESS LEAD FOR HEART FAILURE PACING

BACKGROUND OF THE INVENTION

I. Field of the Invention

This invention relates generally to an electrical cardiac pacing and/or sensing lead and a method of treating heart failure using such lead to optimize hemodynamic performance of a sick heart. More particularly, this invention relates to an elongated, thin, flexible lead having a laser banded electrode surface adapted for placement in a selected coronary vein. The lead may include a transition ring that further assists the user in guiding the lead through a coronary vein. Also, a method is provided for delivering a lead to a predetermined region of a patient's heart and then stimulating the left ventricle, without a need for implanting a pacing lead within the left ventricular chamber.

II. Discussion of the Related Art

In the past, transveneously inserted leads for implantable cardiac pacemakers have principally been positioned within the right atrium or right ventricle of the patient's heart for pacing the right atrium and/or right ventricle, respectively. While it is relatively safe to insert a pacing lead and associated electrode(s) into the right atrium or right ventricle, there is a reluctance to install a similar lead into the left ventricle because of the possibility of clot formation and resulting stroke.

When a lead is implanted within a patient's circulatory system, there is always the possibility of a thrombus being generated and released. If the lead is positioned in the right atrium or right ventricle, a generated thrombus tends to migrate through the pulmonary artery and is filtered by the patient's lungs. A thrombus generated in the left atrium or left ventricle, however, would pose a danger to the patient due to the possibility of a resulting ischemic episode.

Thus, in those instances where left heart stimulation is desired, it has been a common practice to use an intercostal approach using a myocardial screw-in, positive-fixation lead. The screw-in lead may, however, be traumatic for the patient. There are additional instances when left ventricular pacing is desired, such as during bi-ventricular pacing. Mower, in U.S. Pat. No. 4,928,688 (hereinafter "the '688 patent"), describes an arrangement for achieving bi-ventricular pacing in which electrical stimulating pulses are applied, via electrodes on a single pacing lead, to both the right and left ventricular chambers so as to obtain a coordinated contraction and pumping action of the heart. The '688 patent discloses a split pacing lead having first and second separate electrodes, wherein the first electrode is preferably introduced through the superior vena cava for pacing the right ventricle and the second electrode is introduced through the coronary sinus for pacing the left ventricle. The lead and method described in the '688 patent is limited in placement of the second electrode within the coronary sinus. Hence, there is a need for a lead having a construction suitable for placement in the coronary veins including the posterior veins, the middle veins or the great vein.

Other electrode leads which are inserted into the coronary sinus have been described. For example, in U.S. Pat. No. 5,014,696 to Mehra and U.S. Pat. No. 4,932,407 to Williams there is disclosed an endocardial defibrillation electrode system. They each disclose transveneously inserting an electrode lead into the coronary sinus and great vein of a patient's heart, but in each case the lead does not extend through the great vein downward towards the apex of the heart. The leads disclosed by Mehra and Williams are limited to use in conjunction with either another lead inserted in the right ventricle or a large subcutaneous surface patch electrode in order to apply a defibrillating shock to a patient's heart.

A lead and method suitable for pacing the left ventricle of a patient's heart in accordance with the present invention is not disclosed in the related art. The related art does not disclose a lead that may be used to improve the synchronization and/or coordination of the contraction of the chambers of the heart or pace all four chambers of the heart with two leads, wherein the lead has a laser banded electrode surface adapted for placement in a selected coronary vein. Also, the current leads may not be easily rotated and guided into the coronary vein of a patient. Hence, a need exists for a lead and method of pacing a patient's heart to achieve a desired synchronization, wherein the lead has a diameter, flexible tip and physical properties and rotational ability suitable for positioning it in any of several coronary veins, to thereby selectively pace the left ventricle, left atrium, right atrium or a combination thereof The present invention meets these needs and overcomes other disadvantages of the prior art.

SUMMARY OF THE INVENTION

In accordance with the present invention, a coronary vein lead is provided which may be selectively positioned in any one of the several coronary veins to thereby allow selective pacing or sensing of the left ventricle or left atrium without the need for the placement of a pacing lead within the selected ventricle or atrium. The coronary vein lead includes an elongated main body, a flexible tip, a plurality of electrode surfaces, and conductors coupling the electrode surfaces to terminal pins.

The coronary vein lead may be adapted for receiving a stylet or guidewire within a lumen formed along the central longitudinal axis of the lead. The lead may further include a flexible tip and transition ring positioned in the distal portion of the lead, wherein the tip and transition ring assists the user in guiding and rotating the lead through a coronary vein. The method of positioning the coronary vein lead at a desired position within a preselected coronary vein may include the use of a guide catheter, guide wire and support catheter.

For patients with heart failure, a need exists for a lead and method of pacing that will improve the synchronization and/or coordination of the contraction of the chambers of the heart. Improvement in coordination can be achieved by simultaneous or differential stimulation of the left ventricle in relation to stimulation or intrinsic contraction of the right ventricle or in relation to stimulation/intrinsic contraction of either the right or left atria as well as the right ventricle.

Improvement in coordination of the heart's intrinsic contractions can also be achieved by simultaneous or differential pacing of multiple sites on the left ventricle to optimize the contraction of the left ventricle with respect to the other chambers of the heart. A preferred embodiment of the present invention includes the method of placing a lead of the present invention through the coronary sinus and into a coronary vein with one electrode surface positioned in the anterior branch of the great coronary vein near the apex of the left ventricle and a second electrode surface aligned inside the entrance of the coronary sinus near the base of the left ventricle.

With a suitable pacemaker and a right ventricular lead of known construction, coordinated contraction of the right and left sides of the heart are achievable by first pacing the left ventricular apex and then after delays (approximately between 0–50 milliseconds) stimulating the right ventricle and the base of the left ventricle. This method of pacing demonstrates the means by which a lead in accordance with the present invention and a method of pacing the patient's heart will achieve a desired synchronization, wherein the lead has a diameter and physical properties including a flexible tip and transition ring suitable for positioning and rotating the lead in any of several coronary veins, to thereby selectively pace the left ventricle, left atrium or multiple sites on the left atrium or left ventricle.

The method for pacing in accordance with the present invention begins with the physician inserting a guide catheter through the coronary sinus. Once the guide catheter is positioned within the coronary sinus the coronary vein lead of the present invention is inserted through the guide catheter and into a coronary vein associated with a desired heart chamber to be paced. The coronary vein lead preferably includes a lumen for receiving a stylet or guidewire which is removed from the lumen of the coronary vein lead after the electrodes of the lead are properly positioned adjacent predetermined chambers of the heart.

Alternatively, the physician may insert a guide catheter through the superior vena cava into the ostium of the coronary sinus. A guide wire is then inserted into the guide catheter and advanced to the desired position within in a preselected coronary vein. Once the guide wire is in position, a thin walled support catheter is advanced over the guide wire to the distal end of the guide wire. The guide catheter and guide wire are then removed, leaving the support catheter in place. Then, the coronary vein lead of the present invention is advanced through the support catheter to the desired site in the coronary vein. A flexible stylet or guide wire within the coronary vein lead provides axial stiffness to the lead as it is advanced through the support catheter. Once the coronary vein lead is in position, the stylet is used to keep the lead in its desired position within the coronary vein as the support catheter is retracted or peeled away from the lead body.

The coronary vein lead may be constructed in accordance with any of several embodiments, wherein the outer diameter of the coronary vein lead is between 0.023 and 0.092 inches (approximately between a 2–7 French). The coronary vein lead preferably includes a plurality of electrode surfaces spaced longitudinally such that a properly aligned lead may be used to pace or sense, for example, the left atrium, left ventricle and right atrium from more proximally positioned electrodes. By providing several electrode surfaces on the distal end portion of the lead, the physician may utilize a programmable switch in the pacer to select a particular electrode for unipolar pacing or a particular pair for bipolar pacing of, for example, the left ventricle, to optimize the contraction of the heart.

A transition ring may be positioned within the lumen of the coronary vein lead, proximal to the distal end of the lead. The transition ring has a slot or other geometric shape adapted to receive a mating blade or geometric shape formed on an exterior surface of the guidewire, to thereby assist the physician in rotating a distal end of the lead by rotating the proximal end of the guidewire. After the stylet is removed, the guide catheter is removed. The operator may then insert and position other coronary vein leads, depending upon the desired pacing or sensing modality desired. The terminal ends of the coronary vein leads are then coupled to a cardiac pacer, whereby pacing pulses can be applied to the corresponding chambers of the patient's heart.

To further assist the physician in guiding the lead through a coronary vein, a flexible tip may be formed on the distal end of the lead. The flexible tip may include an outer sheath having a biomedical steroid impregnated to the sheath for reducing inflammatory responses of the patient's heart tissue to the presence of the flexible tip. The tip may further be constructed to include an inner cylindrical cable mesh surrounded by the outer sheath, wherein the cable mesh is designed to provide stability and flexibility to the rounded tip.

It is accordingly a principal object of the present invention to provide an apparatus and method of pacing a preselected chamber of a patient's heart from a novel lead disposed in a coronary vein.

Another object of the present invention is to provide a lead having a plurality of electrode surfaces and method of utilizing the lead to pace the left ventricle from a cardiac vein of the patient's heart.

Still another object of the present invention is to provide an apparatus and method for pacing the left ventricle at various positions relative to the apex of the heart to thereby optimize pacing of the left ventricle of the patient's heart.

Yet another object of the present invention is to provide a rotatable, flexible tip lead having a laser banded electrode surfaces and a method thereof utilizing the lead to pace the left ventricle at several sites simultaneously or sequentially and/or in concert with stimulation of the right ventricle, thereby improving contraction of the right and left sides of the heart.

These and other objects, features and advantages of the present invention will be readily apparent to those skilled in the art from a review of the following detailed description of the preferred embodiment in conjunction with the accompanying drawings in which like numerals in the several views refer to corresponding parts.

DESCRIPTION OF THE DRAWINGS

FIG. 1 is an enlarged fragmentary perspective view of a coronary vein lead having a single electrode;

FIG. 2 is an enlarged fragmentary sectional view of a lead of the type of the present invention having a conductor coiled within the lumen of the lead;

FIG. 3 is an enlarged fragmentary view of a longitudinal section of an alternate coronary vein lead having an outer diameter of approximately 0.023 inches;

FIG. 17 is a flowchart showing the method of pacing a patient's heart with a coronary vein lead.

DETAILED DESCRIPTION OF THE PREFERRED EMBODIMENT

Figure 4:
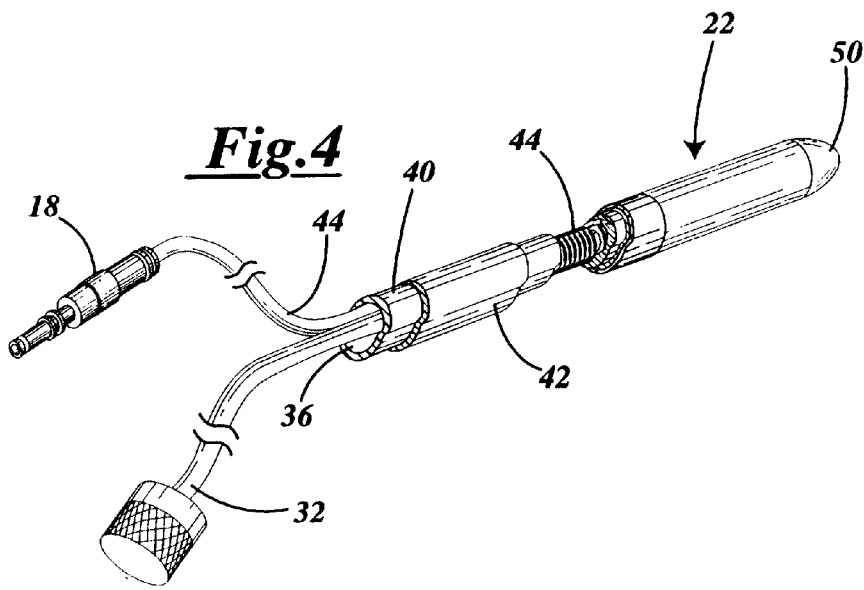
FIG. 4 is an enlarged fragmentary partial sectional perspective view of a lead of the type of the present invention having a stylet inserted therein.

Referring first to FIGS. 1 and 2, there is shown a coronary vein lead 10 specially adapted for use in connection with a cardiac pacemaker, and designed for pacing the left ventricle from one of the heart's posterior veins, middle veins, or great vein. The coronary vein lead 10 includes an elongated main body 12, rounded tip electrode 14, conductor 16, and terminal pin 18. The elongated main body 12 has a proximal end 20, a distal end 22 and a lumen 24 extending longitudinally therethrough. The body 12 is preferably formed from a medical grade polymeric material such as silicone rubber, however limitation to that particular material is not intended. Without any limitation intended, the main body has a thickness of between 0.004 and 0.010 inches, whereby the outer diameter of the main body 12 ranges between 0.023 to 0.092 inches.

As seen in FIG. 3, an outer layer or sleeve 34 may surround the main body 12. Without any limitation intended, the sleeve 34 may be constructed from a carbon coated silicone, steroid eluting silicone, or a combination of silicone and an anti-fibrotic surface treatment element. Any of these compositions help reduce tissue response to the lead insertion, so that the lead will not cause clots or adhesions to the vessel wall, thereby allowing retraction of the lead if necessary in the future. The compositions may also help to prevent encapsulation of the electrode, thereby enhancing the effectiveness of the pacing and sensing capabilities.

Referring again to FIGS. 1 and 2, the conductor 16 is helically wound and fixed within the longitudinal lumen 24 of the main body 12. A distal end 26 of conductor 16 is attached to the rounded tip electrode 14 and the proximal end is attached to the terminal pin 18 by crimping or laser weld known to those skilled in the art. Without any limitation intended, the tip electrode 14 and terminal pin 18 of known construction are manufactured from titanium or platinum plated titanium. The conductor 16 is preferably comprised of a conductive cable, dip coated or spray coated with a polymer such as polytetrafluoroethylene, however, limitation to that particular material is not intended. The fabrication and construction of the conductive cable is disclosed in Dahl et al. U.S. Pat. No. 4,559,951, the disclosure of which is incorporated herein by reference in its entirety. The coated conductor has an outer diameter of 0.004 to 0.005 inches and is helically wound. A lumen 30 is formed within the helically wound conductor 16, having an inner diameter between 0.007 and 0.020 inches, wherein a stylet 32 of known construction (shown in FIG. 4) having an outer diameter between 0.006 and 0.018 inches is positioned within lumen 30.

In the embodiment shown in FIG. 3, the helically coiled conductor 16 is embedded in the 0.001 inch thick polymer main body 12, thereby eliminating the need for coating the conductor. The main body has a central lumen with an inner diameter between 0.007 and 0.020 inches and the outer sleeve 34 encompasses the main body 12. The stylet 32 (generally shown in FIG. 4) is adapted to be disposed in the central lumen of the main body 12, and utilized as an angioplasty guide wire.

Figure 5:
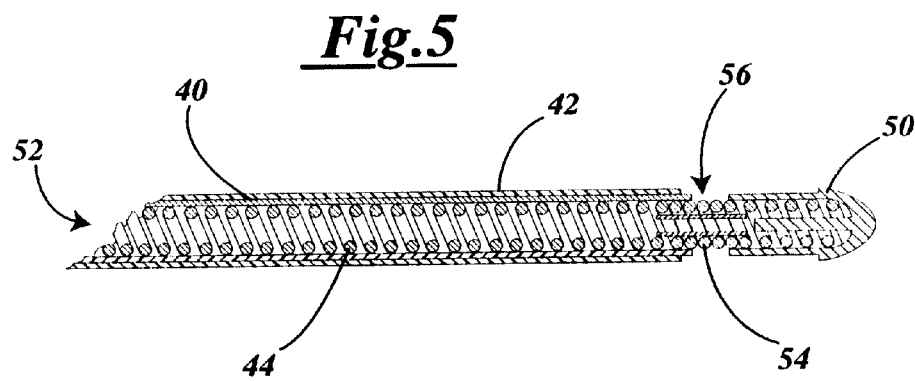
FIG. 5 is an enlarged fragmentary sectional view of the coronary vein lead of the present invention having a laser banded conductor coil electrode.

FIGS. 4 and 5 shows the preferred embodiment of the coronary vein lead 10. This embodiment includes a main body 40, longitudinal sleeve 42, helically coiled conductor 44, and a tip 50. The lead 10 is shown having a distal end portion of the stylet 32 (as described above) aligned with a longitudinal lumen 52 formed by the helically coiled conductor 44. The distal end of conductor 44 extends to the rounded tip 50 and the proximal end is connected to a terminal pin of known construction.

Proximate the distal end of the main body 40, a window 56 is formed within the main body 40 and sleeve 42 of the lead adjacent a central portion of the conductor 44. The conductor coil 44 exposed in the window 56 is fused or melted together by laser or other known means to create the electrode surface 54. Those skilled in the art will recognize that a ring electrode could be substituted and attached to the conductor as described in U.S. Pat. No. 4,559,951, the disclosure of which is incorporated herein by reference, however, the laser banded electrode surface is preferred.

As described above, the conductor 44 may alternatively be embedded within the main body 40. Without any limitation intended, the outer diameter of the main body 40 may be between 0.023 to 0.092 inches, wherein the thickness of cylindrical wall of the main body 40 is between 0.007 and 0.010 inches. In the embodiment shown in FIGS. 4 and 5, the window 56 and exposed electrode surface 54 are spaced a predetermined distance from the distal end of the lead, whereby, after placement of the lead 10 the electrode surface 54 is aligned in a coronary vein adjacent a predetermined portion of the left ventricle.

Those skilled in the art will appreciate that an electrode tip could replace tip 50, positioning the tip in distal end of the lead and attaching the electrode tip to a separate independantly insulated conductor coil wound together with conductor coil 44, whereby the electrode surface 54 could be positioned near the tip electrode, such that the electrodes could be used for sensing or bi-polar pacing. The pacing signal could then be sent simultaneously or sequentially to the electrode surface 54 and tip electrode. Alternatively, the tip electrode could be excluded entirely so that unipolar pacing is possible between the electrode surface and the pacemaker can. In such a case, the tip 50 may comprise a continuous insulative polymer, carbon coated silicon polymer or other anti-fibrotic attachment surface treatment, thereby enclosing the distal end of the main body 40 and conductor coil 44.

Figure 6:
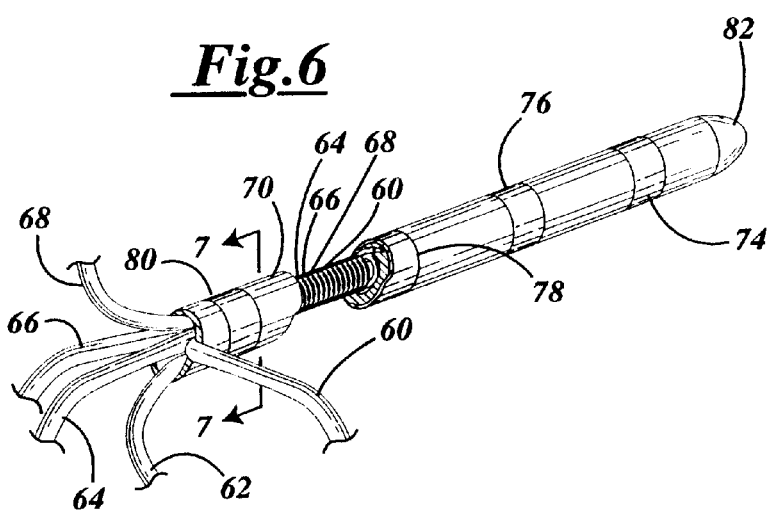
FIG. 6 is an enlarged fragmentary partial sectional perspective view of an alternate coronary vein lead of the present invention having five ring electrodes.
Figure 7:
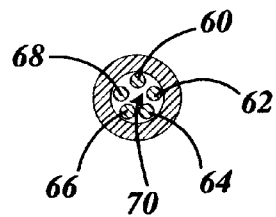
FIG. 7 is a cross-sectional view taken along line 7—7 of FIG. 6.
Figure 8:
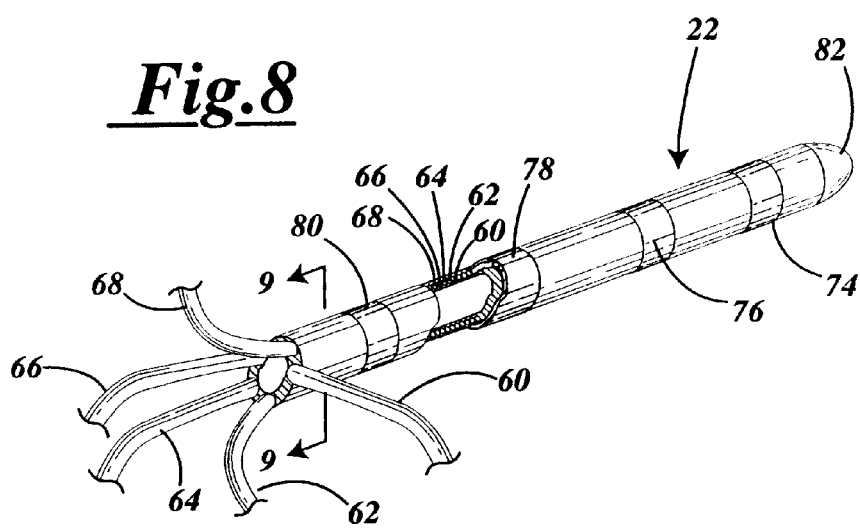
FIG. 8 is an enlarged fragmentary partial sectional perspective view of an alternate coronary vein lead of the present invention having five electrodes.
Figure 9:
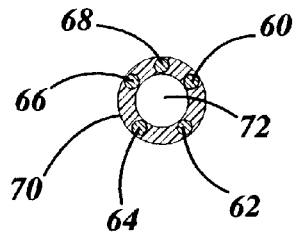
FIG. 9 is a cross-sectional view taken along line 9—9 of FIG. 8.

Referring now to FIGS. 6 and 7, another embodiment of the coronary vein lead 10 is shown. In this embodiment, five independently insulated conductors 60–68 are shown helically coiled extending through the lumen 72 of the main body 70. Each conductor 60–66 is coupled to a corresponding electrode ring 74–80 (as described above), and conductor 68 is coupled to the rounded tip electrode 82. In the embodiment shown in FIGS. 8 and 9, the insulated conductors 60–68 are shown helically coiled and embedded within the main body 70, whereby the central longitudinal lumen 72 is adapted for receiving stylet 32.

Figure 10:
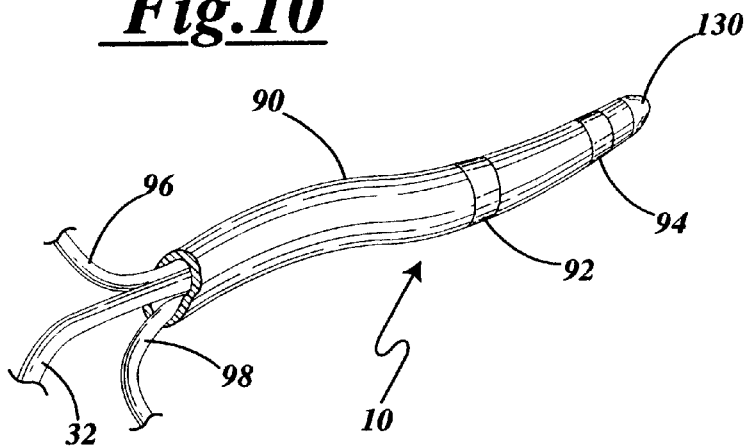
FIG. 10 is an enlarged fragmentary perspective view of a tapered alternate coronary vein lead of the present invention having three electrodes.

FIG. 10 shows an alternate coronary vein lead 10 having a tapered main body 90 (the taper is shown exagerated), wherein the main body 90 begins to taper to a lesser diameter near the distal end of main body 90. Tapered ring electrodes 92 and 94 corresponding with the taper of the main body 90 are molded in the main body 90 along the tapered portion near the distal end of the main body 90. Conductors 96 and 98 linking the electrodes 92 and 94 to terminal pins of known construction are helically coiled within the main body 90 as previously described.

Figure 11:
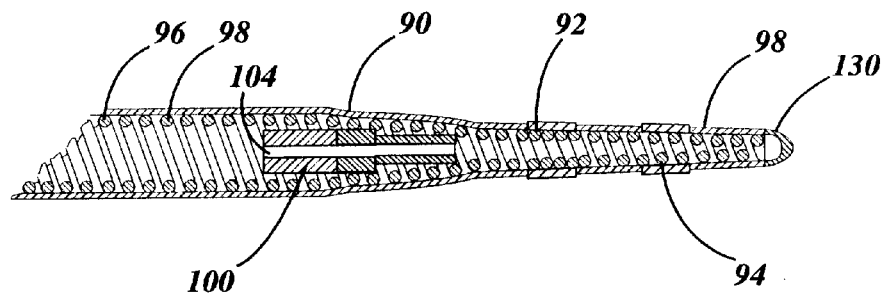
FIG. 11 is an enlarged fragmentary side elevational sectional view of a tapered portion of a coronary vein lead of the type shown in FIG. 10, showing a transition ring positioned within the taper.
Figure 12:
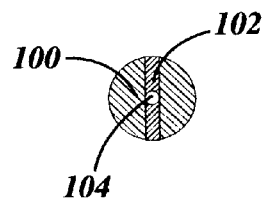
FIG. 12 is an end elevational view of the transition ring of the type shown in FIG. 11.

FIG. 11 is a sectional view of the lead of the type shown in FIG. 10 illustrating a transition ring 100 crimped or welded to the conductors 96 and 98 and positioned within the taper. The transition ring 100 includes a slot 102 formed on the proximal end thereof, and a lumen 104 extending along the longitudinal axis therethrough (see FIG. 12). A stylet or guide wire (as described above) used to guide the lead has a smaller diameter section that extends to the tip of the lead through the lumen 104 of the transition ring 100. A stiffer, wider diameter section of the stylet may be flattened along a portion to form a blade which aligns and engages with the slot 102 of the transition ring 100, when the stylet is fully inserted within the lumen of the lead. By turning the proximal end of the stylet, a physician may rotate and steer the distal end of the lead, thereby enhancing the steerability of the smaller tapered portion of the lead 10.

Those skilled in the art will appreciate that the transition ring 100 may be positioned either closer or further from the distal tip of the lead 10. By positioning the transition ring 100 closer to the distal tip of the lead 10, more control over the position of the tip may be attained. The slot 102 formed on the end of the transition ring 100 may alternatively take any of several geometrically shaped sockets including without limitation a square, triangle or hexagon. Hence, the transition ring of the present invention may likewise be adapted for placement within the distal end of a lead of known construction, thereby increasing the ability to guide the lead.

Figure 13:
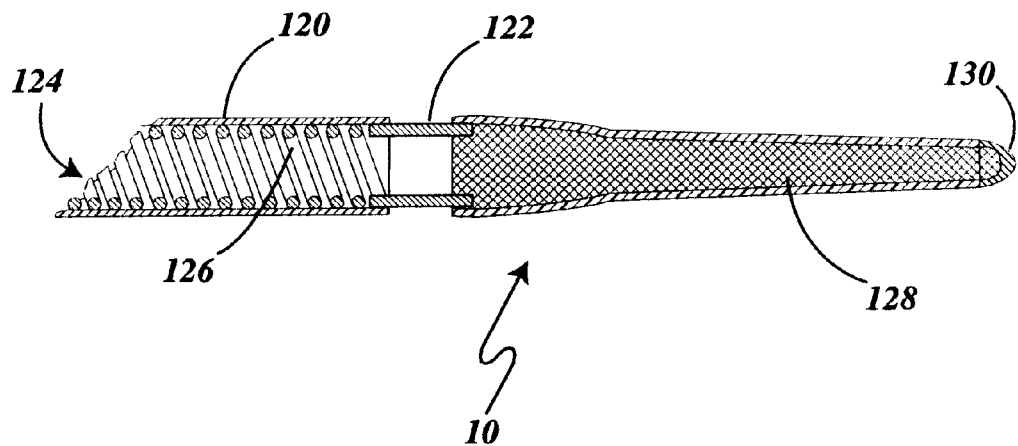
FIG. 13 is an enlarged fragmentary side elevational sectional view of an alternate embodiment of the flexible tip of the lead of the present invention.

FIG. 13 is yet another embodiment of the lead 10 suitable for placement in a coronary vein having a ring electrode 122. The lead 10 has a main body 120, lumen 124, conductor 126, and a wire mesh 128 attached and extending from the distal end of the electrode 122. A rounded flexible tip 130, surrounding the wire mesh 128, is formed by an outer flexible polymer sheath. The sheath has a biomedical steroid impregnated to said sheath for reducing inflammatory responses of the patient's heart tissue to the presence of the flexible tip. The wire mesh 128 is cylindrical in shape and is designed to provide stability yet flexibility to the rounded tip. Referring to FIG. 11, a similar flexible tip is shown wherein the conductor 98 extends distally beyond the ring electrode 94. In this configuration, the conductor 98 is surrounded by the impregnated polymer flexible tip 130, and is a substitute for the wire mesh 128, providing stability yet flexibility to the rounded tip 130.

Figure 14:
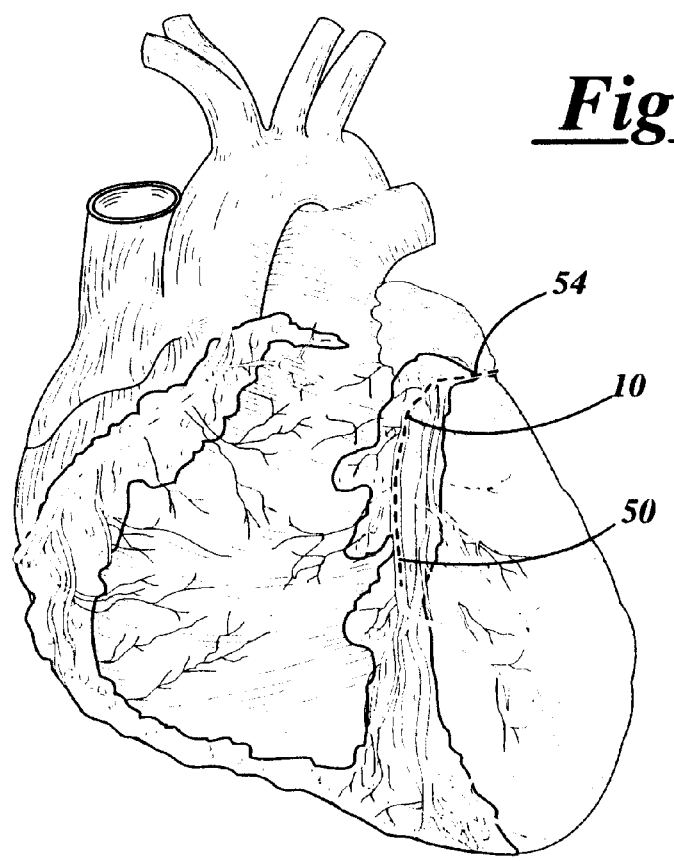
FIG. 14 is a perspective view of a coronary vein lead of the present invention shown positioned within the anterior cardiac vein of a patient's heart.
Figure 15:
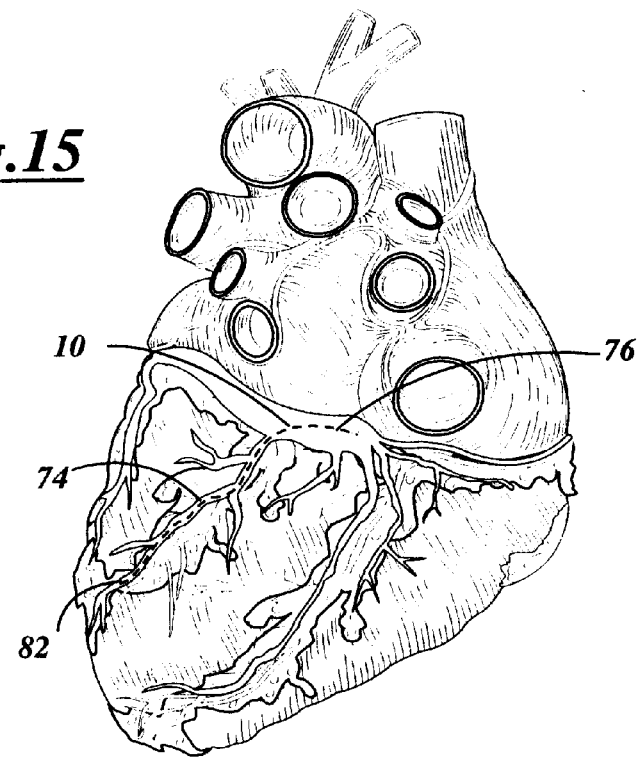
FIG. 15 is a perspective view of a coronary vein lead of the present invention shown positioned within the posterior cardiac vein of a patient's heart.
Figure 16:
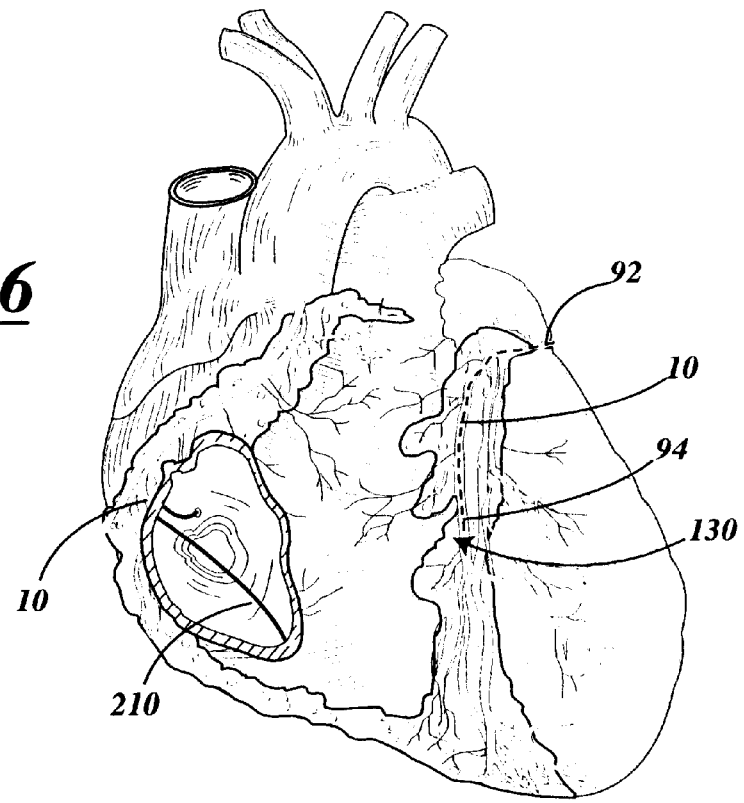
FIG. 16 is a partial sectional perspective view of a coronary vein lead of the present invention shown positioned within the anterior cardiac vein and a right ventricular lead shown positioned in the right ventricle.

FIGS. 14–16 illustrates the positioning of coronary vein leads within a patient's coronary veins for various methods of pacing. FIG. 14 shows a coronary vein lead 10 similar to that shown in FIG. 4 with the distal end and rounded tip 50 aligned with the left ventricle (positioned within the anterior cardiac vein) and the laser banded electrode 54 aligned with the left atrium. The lead 10 is connected to a cardiac pacer (not shown) for independent pacing of the left ventricle. FIG. 15 shows a coronary vein lead 10 similar to that shown in FIGS. 6 and 7 with the distal end of the tip electrode 82 aligned with the left ventricle (positioned within a posterior cardiac vein) wherein electrode ring 76 is aligned with the left atrium. The lead 10 is connected to a cardiac pacer (not shown) for independent pacing of the left ventricle and left atrium. FIG. 16 shows a coronary vein lead 10 similar to that shown in either FIGS. 11–12 or FIG. 13, with the distal end of the rounded flexible tip 130 aligned with the left ventricle (positioned within the anterior cardiac vein), a first electrode 92 aligned with the left atrium, a second electrode 94 aligned with the left ventricle, and a second lead 210 extending into the right ventricle. The leads are connected to a cardiac pacer (not shown) for independent pacing of the left ventricle, left atrium, and right ventricle. Of course a third electrode could be positioned on the lead to thereby align with the right atrium to allow independent pacing of the left ventricle, left atrium, right ventricle, and right atrium.

Having generally explained the features and positioning of the coronary vein lead 10, referring to the flow diagram of FIG. 17, the various methods of pacing a patient's heart using a coronary vein lead 10 will now be discussed. The method of pacing a patient's heart identified in the flow chart of FIG. 17 allows the user to effectively pace the left ventricle without the increased risk of an ischemic episode.

The operator first positions a guide catheter, of the tear away type known to those skilled in the art, within the coronary sinus (block 150). Although the use of a guide catheter is not absolutely necessary, the guide catheter increases the ability of the operator to properly position the coronary vein lead 10 within a preselected coronary vein. Once the guide catheter has been positioned within the coronary sinus, the coronary vein lead 10 is inserted through the lumen of the guide catheter and into a predetermined coronary vein under fluoroscopic observation (see Block 152). The coronary vein lead 10 is positioned within the selected coronary vein, wherein the electrodes of the coronary vein leads 10 are aligned with the selected chambers to be paced. Those skilled in the art will appreciate that the electrodes may be constructed from a radiopaque material such that the position of the electrode is readily determined. After the coronary vein lead 10 is positioned, the stylet or guide wire (if present) is removed from the coronary vein lead (block 154). The catheter is then removed from the coronary sinus (block 156), whereby the catheter is torn away as the catheter is pulled past the terminal pins of the coronary lead 10. As noted above, a guide catheter may be used to direct a guide wire which is used to guide a support catheter to a desired position within a preselected coronary vein. The support catheter is then used to position the coronary vein lead 10 as described above.

After the guide catheter has been removed, the operator decides whether there are additional coronary vein leads to be inserted and positioned within the coronary veins of a patient's heart (see decision block 158). If other coronary vein leads 10 are to be positioned within preselected coronary veins, then the above steps represented by blocks 150–156 are repeated (see loop 160). Those skilled in the art will appreciate that an additional lead of suitable construction could be positioned within the right ventricle. If no other coronary vein leads 10 are to be inserted and positioned, then the terminal pins 18 attached to each coronary vein lead 10 are coupled to corresponding terminal ports of a cardiac pacer (block 162). The cardiac pacer is then programmed by known means to transmit a pacing pulse through each coupled coronary vein lead 10 (block 164), thereby pacing the preselected chamber of the patient's heart.

Once the coronary vein leads 10 (of a suitable embodiment) are inserted and positioned, without any limitation intended, the operator has the ability to, for example, pace or sense both the left atrium and left ventricle, pace or sense the left atrium, left ventricle, and right atrium. When a separate right ventricular lead is positioned, pacing and/or sensing from all chambers of the heart is possible. The diameter and construction of the coronary vein lead provides the flexibility necessary to reduce substantially the likelihood that the flexing coronary vein lead 10 will erode through the coronary vein. In this regard, the main body 12 of the coronary vein lead 10 may be coated or impregnated with a biomedical steroid to reduce the inflammatory response of the coronary veins to the insertion and positioning of the coronary vein lead 10 within the coronary vein. The selected biomedical steroid may also be used to reduce the amount of fiber build-up between the coronary vein lead 10 and the coronary vein. The coronary vein lead 10 may be constructed to include an anchoring member whereby the lead 10 could be anchored within the coronary vein or coronary sinus.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of pacing a patient's heart, comprising the steps of:
   a) transveineously inserting and positioning a lead having a proximal end, a distal end, and a lumen, through a coronary sinus and into a coronary vein of a patient's heart, the coronary vein being one of a posterior vein, an anterior vein, a middle vein and a great vein, the lead including an electrode surface disposed on the lead in a zone located near the distal end and a transition ring for transferring a rotational force fixed within the lead;
   b) coupling said electrode surface to a means for pacing the patient's heart; and
   c) applying a pacing pulse from said means for pacing to said electrode surface via said lead to thereby pace the left ventricle of the patient's heart.

2. The method as recited in claim 1, wherein the step of inserting includes introducing the lead into the coronary sinus through a guide catheter.

3. The method as recited in claim 1, wherein the step of positioning includes engaging a blade portion of a stylet within a slot formed in said transition ring.

4. The method as recited in claim 2, further comprising the step of removing the guide catheter after the lead has been inserted through both the coronary sinus and into the coronary vein of the patient's heart.

5. The method as recited in claim 4, wherein said lead further includes a removable guide means having a blade portion that interlocks with a slot of said transition ring for guiding a predetermined distal portion of said lead through the patient's heart, said guide means extending through the lumen of said lead.

6. The method as recited in claim 1, wherein said lead further includes a removable guide means for guiding said lead through the patient's heart, said guide means extending through the lumen of said lead.

7. A method of pacing or sensing in a patient's heart, comprising the steps of:
   a) transveineously inserting a first lead, having at least a first electrode disposed on the first lead in a zone located near a distal end, through a patient's coronary sinus and into a coronary vein at a location adjacent the left atrium of the patient's heart;
   b) transveineously inserting a second lead, having at least a second electrode disposed on the second lead in a zone located near the distal end of said second lead, through the coronary sinus and into a coronary vein adjacent the left ventricle of a patient's heart;
   c) coupling said first and second leads to a means for pacing the patient's heart; and
   d) applying first and second pacing pulses from said means for pacing to said first and second electrodes, thereby performing at least one of pacing and sensing of the left atrium and left ventricle of the patient's heart.

8. The method as recited in claim 7, wherein the steps of inserting the first and second leads includes introducing the first and second leads into the coronary sinus through corresponding guide catheters.

9. The method as recited in claim 8, further comprising the steps of removing the corresponding guide catheters after the first and second leads have been inserted through both the coronary sinus and into the respective coronary veins of the patient's heart.

10. The method as recited in claim 9, wherein each said first and second leads inserted in the coronary veins of a patient's heart further includes a lumen extending a length of each lead and adapted for receiving therein a removable guide means for guiding said lead through the patient's heart.

11. The method as recited in claim 10 further including the step of, removing said guide means after said leads have been inserted through both the coronary sinus and into the respective coronary veins of the patient's heart.

12. The method as recited in claim 7, wherein each said first and second leads further includes a lumen extending a length of each lead and adapted for receiving therein a removable guide means for guiding said lead through the patient's heart.

13. A method of pacing a patient's heart, comprising the steps of:
   a) transveineously inserting and positioning a lead through a coronary sinus and into a coronary vein adjacent the left ventricle of the patient's heart, said lead having a proximal end, a distal end, a lumen, and a transition ring positioned within said lumen for transferring a rotational force from a stylet positioned within the lumen to a predetermined distal portion of said lead, said lead including first and second electrodes disposed on the lead, wherein the first electrode is aligned with the left ventricle and the second electrode is aligned with the left atrium;
   b) coupling said first and second electrodes to a means for pacing the patient's heart; and
   c) applying first and second pacing pulses from said means for pacing to said first and second electrodes, via said lead, to thereby pace the left ventricle and left atrium of the patient's heart.

14. The method as recited in claim 13, wherein the step of inserting includes introducing the lead into the coronary sinus through a guide catheter.

15. The method as recited in claim 14, further comprising the step of removing the guide catheter after the lead has been inserted through both the coronary sinus and into the coronary vein of the patient's heart.

16. The method as recited in claim 14, wherein the stylet further includes a blade portion that interlocks with a slot of said transition ring for guiding the predetermined distal portion of said lead through the patient's heart.

17. The method as recited in claim 13, wherein the step of positioning includes engaging a blade portion of the stylet within a slot formed in said transition ring.

18. A method of pacing a patient's heart, comprising the steps of:
   a) transveineously inserting and positioning a lead through a coronary is sinus and into a coronary vein adjacent the left ventricle of the patient's heart, said lead having a proximal end, a distal end, a lumen, and a transition ring positioned within said lumen for transferring a rotational force from a stylet positioned within the lumen to a predetermined distal portion of said lead, said lead including first, second, and third electrodes disposed on the lead, wherein the first electrode is aligned with the left ventricle, the second electrode is aligned with the left atrium, and the third electrode is aligned with the right atrium;
   b) coupling said first, second and third electrodes to a means for pacing the patient's heart; and
   c) applying first, second, and third pacing pulses from said means for pacing to said first, second and third electrodes, via said lead, to thereby pace the left ventricle, left atrium, and right atrium of the patient's heart.

19. The method as recited in claim 18, wherein the step of inserting includes introducing the lead into the coronary sinus through a guide catheter.

20. The method as recited in claim 19, further comprising the step of removing the guide catheter after the lead has been inserted through both the coronary sinus and into the coronary vein of the patient's heart.

21. The method as recited in claim 19, wherein the stylet further includes a blade portion that interlocks with a slot of said transition ring for guiding the predetermined distal portion of said lead through the patient's heart.

22. The method as recited in claim 18, wherein the step of positioning includes engaging a blade portion of the stylet with a slot formed in said transition ring.

23. The method as recited in claim 18, further comprising the step of transveineously inserting a second lead into the right ventricle, said second lead having an electrode pair disposed on said lead adjacent a distal end, and coupling said electrode pair to said cardiac pacer, for selectively performing at least one of pacing and sensing of at least one of the right atrium, the left atrium, the right ventricle and the left ventricle of the patient's heart.

24. An elongated coronary vein lead for delivering a pacing signal and sensing electrical impulses in a predetermined region of a patient's heart, comprising:
   a) an elongated, flexible, insulative main body portion having a proximal and distal end, wherein the distal end has a rounded tip attached thereto;
   b) a plurality of electrodes mutually insulated and spaced a predetermined distance from one another and embodied within said main body portion;
   c) a plurality of independently insulated conductors, wherein a distal end of each conductor is attached individually to a corresponding one of a plurality of electrodes and a proximal end of each conductor is attached to a corresponding terminal pin, said plurality of independently insulated conductors being helically coiled within said elongated main body portion to define a central lumen;
   d) a transition ring fixed within said central lumen a predetermined distance from said distal end of said lead, said transition ring having an inner lumen extending therethrough and aligned with said central lumen; and
   e) an elongated guide means for guiding the lead through the patient's heart, said guide means interlocking with said transition ring and being removably positioned within the central lumen, for facilitating the routing of the lead body portion into a predetermined coronary vein, a distal end of said elongated guide means being sized to extend through the inner lumen of said transition ring.

25. The lead as recited in claim 24, further comprising a sleeve encompassing said main body, said sleeve having a biomedical steroid impregnated to said sleeve for reducing inflammatory responses of the patient's heart tissue to the presence of the lead body.

26. The lead as recited in claim 24, wherein said main body has an outer diameter ranging between 0.023 to 0.092 inches.

27. The lead as recited in claim 24, wherein said transition ring includes a slot that interlocks with a blade formed on said guide means.

28. The lead as recited in claim 24, wherein the rounded tip is formed around a cylindrical cable mesh to provide stability and flexibility to the rounded tip.

29. The lead as recited in claim 24, wherein the rounded tip is formed from a flexible polymer.

30. The lead as recited in claim 24, wherein one of said plurality of independently insulated conductors extends to a distal end of said main body, thereby forming the rounded tip.

31. An elongated coronary vein lead for delivering a pacing signal and sensing electrical impulses in a predetermined region of a patient's heart, comprising:
   a) an elongated, flexible, insulative main body portion having a proximal and distal end, wherein the distal end has a rounded flexible tip attached thereto;
   b) an insulated conductor being helically coiled within said elongated main body portion to define a central lumen;
   c) said main body having a window formed in said main body, wherein a portion of said conductor is exposed through said window of said main body, said exposed portion being fused to form an electrode surface;
   d) a transition ring fixed within said central lumen a predetermined distance from said distal end of said lead; and
   e) an elongated guide means for guiding the lead through the patient's heart, said guide means interlocking with said transition ring and being removably positioned within the central lumen, for facilitating the routing of the lead body portion into a predetermined coronary vein.

32. The lead as recited in claim 31, further comprising a sleeve encompassing a predetermined portion said main body, said sleeve having a biomedical steroid impregnated to said sleeve for reducing inflammatory responses of the patient's heart tissue to the presence of the lead body.

33. The lead as recited in claim 31, wherein said main body has an outer diameter ranging between 0.023 to 0.092 inches.

34. The lead as recited in claim 31, wherein said transition ring includes a slot that interlocks with a blade formed on said guide means.

35. The lead as recited in claim 31, wherein said rounded flexible tip further comprises an outer sheath having a biomedical steroid impregnated to said sheath for reducing inflammatory responses of the patient's heart tissue to the presence of the flexible tip and further includes an inner cylindrical cable mesh surrounded by said outer sheath, said cable mesh designed to provide stability and flexibility to the rounded tip.

* * * * *